United States Patent [19]
De Briere et al.

[11] Patent Number: 5,782,778
[45] Date of Patent: Jul. 21, 1998

[54] APPARATUS AND METHOD FOR DETECTING AND MONITORING THE SEXUAL AROUSAL OF AN INDIVIDUAL

[75] Inventors: Terry J. De Briere, Ft. Myers, Fla.; Jerry Rea, Parsons, Kans.

[73] Assignee: Parsons State Hospital Endowment Association Inc., Parsons, Kans.

[21] Appl. No.: 736,264

[22] Filed: Oct. 24, 1996

[51] Int. Cl.$^6$ .................................................... A61B 5/00
[52] U.S. Cl. ................................. 600/587; 600/595
[58] Field of Search ........................... 128/774, 782; 33/511, 512

[56] References Cited

U.S. PATENT DOCUMENTS

| | | | |
|---|---|---|---|
| 4,509,531 | 4/1985 | Ward | 128/736 |
| 4,848,361 | 7/1989 | Penney et al. | 128/774 |
| 5,537,102 | 7/1996 | Pinnow | 340/825.3 |

OTHER PUBLICATIONS

Brochure—Mercury Strain Gage Plethysmograph, Model 240-A—Parks Medical Electronics, Aloha, Oregon, 1985.
Brochure—The Portable CAT-600A Sex Offender Assessment System from Behavioral Technology, Inc., Salt Lake City, Utah—1995.
Article—Sexual offenders against female children: Sexual preferences for age of victims and type of behavior—by W.L. Marshall, H.E. Barbaree, and D. Christophe, Queens University; Canad. J. Behav. Sci/Rev. Canad: Sci. Comp. 18-(4), 1986, pp. 424–439.
Article—Biofeedback and Signaled Punishment in the Modification of Inappropriate Sexual Age Preferences—by Vernon L. Quinsey, Terry C. Chaplin and Wayne F. Carrigan of Oak Ridge Division, Mental Health Centre, Penetanguishene, Ontario; Behavior Therapy 11, pp. 567–576 (1980).
Article—Treatment of bisexual pedophilia by a biofeedback–assisted self–control procedure—D. R. Laws, Sexual Behavior Laboratory, Atascadero State Hospital, Atascadero, California; Behr. Res & Therapy, vol. 18, pp. 207–211, Pergamon Press Ltd 1980.

*Primary Examiner*—Max Hindenburg
*Attorney, Agent, or Firm*—Hovey,Williams, Timmons & Collins

[57] ABSTRACT

An apparatus (10) and method for detecting and monitoring the sexual arousal of an individual while the individual is exposed to real-life sexual stimuli outside of a clinical or laboratory setting is disclosed. The apparatus (10) includes a physiological sensor (12) for sensing physiological changes in the individual that correspond to the sexual arousal of the individual and for generating sensor signals representative of the physiological changes; a microprocessor (14) coupled with the sensor (12) for receiving the sensor signals, converting the sensor signals to control signals representative of the sensor signals, and storing the control signals; and a transmitter (16) coupled with and responsive to the microprocessor (12) for transmitting the stored control signals to an analyzing device remote from the apparatus (10) for analyzing the control signals to monitor the sexual arousal of the individual.

39 Claims, 1 Drawing Sheet

APPARATUS AND METHOD FOR DETECTING AND MONITORING THE SEXUAL AROUSAL OF AN INDIVIDUAL

SOURCE CODE APPENDIX

An appendix containing the source code of a computer program useful in the present invention is appended hereto.

BACKGROUND OF THE INVENTION

1. Field of the Invention

The present invention relates to devices for assessing and treating sexual offenders and patients suffering from sexual disorders. More particularly, the invention relates to an apparatus and method for detecting and monitoring the sexual arousal of an individual while the individual is exposed to real-life sexual stimuli outside of a clinical or laboratory setting.

2. Description of the Prior Art

Devices for detecting and monitoring physiological changes of an individual that correspond to the sexual arousal of the individual are known in the art. For example, penile plethysmographs are commonly used by therapists and correctional professionals to detect changes in the penile circumference or length of a male sexual offender when the offender is exposed to sexual stimuli. These physiological changes are analyzed to assess which stimuli cause sexual arousal in the offender for use in treating or rehabilitating the sexual offender. Similarly, these types of devices are sometimes used for assessing and treating non-criminal sexual disorders such as impotence.

Unfortunately, known sexual arousal detecting and monitoring devices are large and cumbersome and therefore must be used in controlled clinical or laboratory settings. The devices typically include a physiological sensor for measuring a physical parameter of the individual and a full-size computer electrically coupled with the sensor for converting, analyzing and displaying the sensor signals. In use, the sensor is first attached to the individual being monitored. The individual is then placed in a lab or monitoring room and exposed to sexual stimuli provided by audio tapes or video cassettes. The signals generated by the sensor are transferred to the computer, which is placed in a nearby control room, and compared with the sexual stimuli to determine which stimuli causes sexual arousal in the individual.

Since these prior art devices must be used in controlled clinical or laboratory settings, they cannot accurately assess the transfer of treatment effects from the laboratory to real-life sexual stimuli in a normal environment. In addition, the controlled clinical setting and pre-recorded stimuli may diminish or otherwise affect the sexual arousal of the individual and therefore affect the results of the testing.

SUMMARY OF THE INVENTION

The present invention solves the above-described problems and provides a distinct advance in the art of sexual arousal detecting and monitoring devices and methods. More particularly, the present invention provides an apparatus and method for detecting and monitoring the sexual arousal of an individual while the individual is exposed to real-life sexual stimuli outside of a clinical or laboratory setting.

The apparatus of the present invention broadly includes sensing means for sensing physiological changes in an individual that correspond to the sexual arousal of the individual and for generating sensor signals representative of the physiological changes; computing means coupled with the sensing means for receiving the sensor signals, for converting the sensor signals to control signals representative of the sensor signals, and for storing the control signals; and transferring means coupled with and responsive to the computing means for transferring the control signals stored in the computing means to an analyzing device remote from the apparatus for analyzing the control signals to monitor the sexual arousal of the individual.

The apparatus is designed to be stored in a bag such as a fanny pack worn by the individual. Since the control signals are stored and then periodically transmitted to a remote analyzing device, the apparatus can be used to gather sexual arousal data while the individual is in a normal environment outside of a clinical or laboratory setting to detect and monitor the sexual arousal of the individual caused by real-life stimuli.

In preferred forms, the apparatus also includes position detecting means, audio feed-back means, and manually activated analog input means. The position detecting means detects the position of the individual and transfers position signals to the computing means. The computing means then periodically or continuously transfers the position signals to the transmitting means for transmitting the position signals to a remote monitoring station. This permits a therapist or correctional professional to locate the individual whenever the transmitted control signals indicate that the individual has become sexually aroused.

The position detecting means also permits the therapist or correctional professional to enter into the apparatus certain areas that the patient is prohibited from entering into. Then, if the individual enters these prohibited areas, the position detecting means and the audio feed-back means described below cooperate to warn the individual that they are entering a prohibited area.

The audio feed-back means provides an audible signal to the individual whenever the sensor means and computing means determine that the individual is becoming sexually aroused. The individual can then be taught to reduce their arousal to whatever stimuli is causing the sexual arousal.

The manually activated input means permits the individual to assess his or her own sexual arousal level and to input an analog signal representative of this sexual arousal level into the computing means. This provides for self-reporting of the sexual arousal of the individual.

BRIEF DESCRIPTION OF THE DRAWING FIGURES

A preferred embodiment of the present invention is described in detail below with reference to the attached drawing figures, wherein:

FIG. 1 is a block diagram illustrating the components of a sexual arousal detecting and monitoring apparatus constructed in accordance with a preferred embodiment of the invention; and FIG. 2 is a perspective view of a strain gauge plethysmograph-type physiological sensor that may be used with the present invention.

DETAILED DESCRIPTION OF THE PREFERRED EMBODIMENTS

Figure 1:
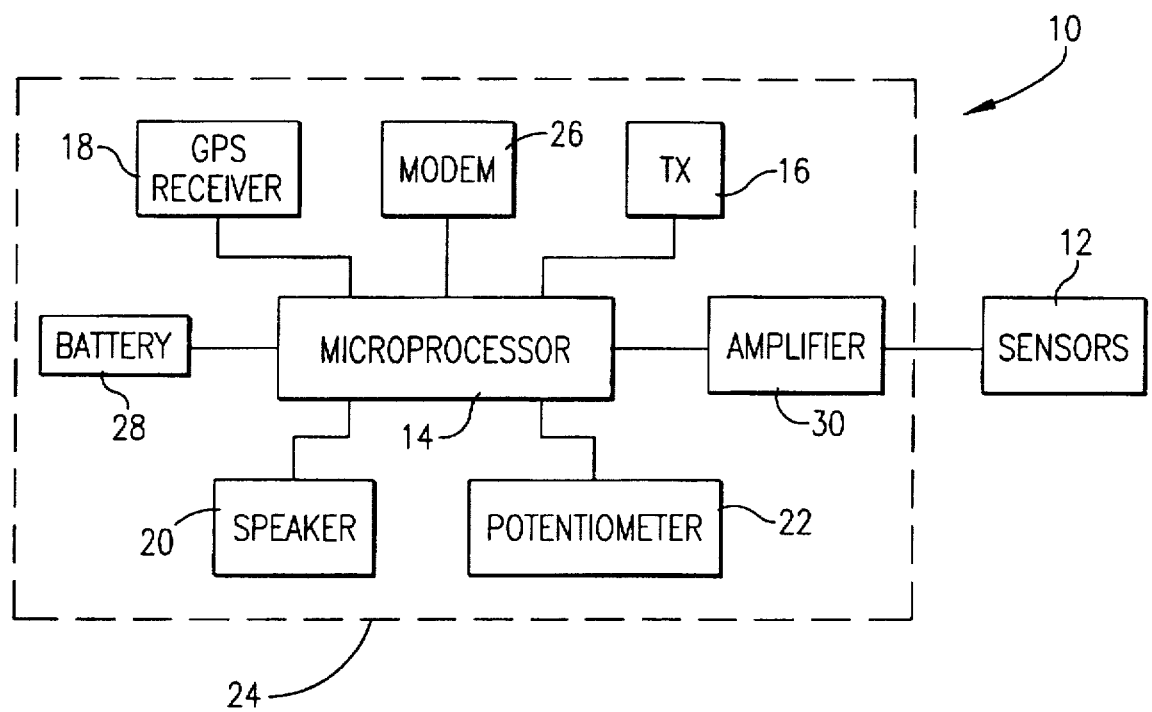

Turning now to the drawing figures, and particularly FIG. 1, a sexual arousal detecting and monitoring apparatus 10 constructed in accordance with a preferred embodiment of the invention is illustrated. Apparatus 10 detects and monitors the sexual arousal of an individual such as a sexual offender or a patient suffering from a non-criminal sexual disorder such as impotence for rehabilitating the sexual offender or treating the patient.

Apparatus 10 broadly includes physiological sensor 12, microprocessor 14, transmitter 16, position detector 18, audio feed-back 20, and manually activated analog input 22. The components of apparatus 10 are preferably stored in bag 24 such as a fanny pack worn by the individual. This permits the individual to move unrestrictedly in his or her normal environment while apparatus 10 remains operably attached to the individual for detecting and monitoring the sexual arousal of the individual while the individual is exposed to real-life sexual stimuli.

In more detail, sensor 12 is configured to be attached to or worn by an individual for sensing physiological parameters or changes in the individual that correspond to the sexual arousal of the individual. Once attached to the individual, sensor 12 generates sensor signals representative of the physiological parameters or changes.

Figure 2:
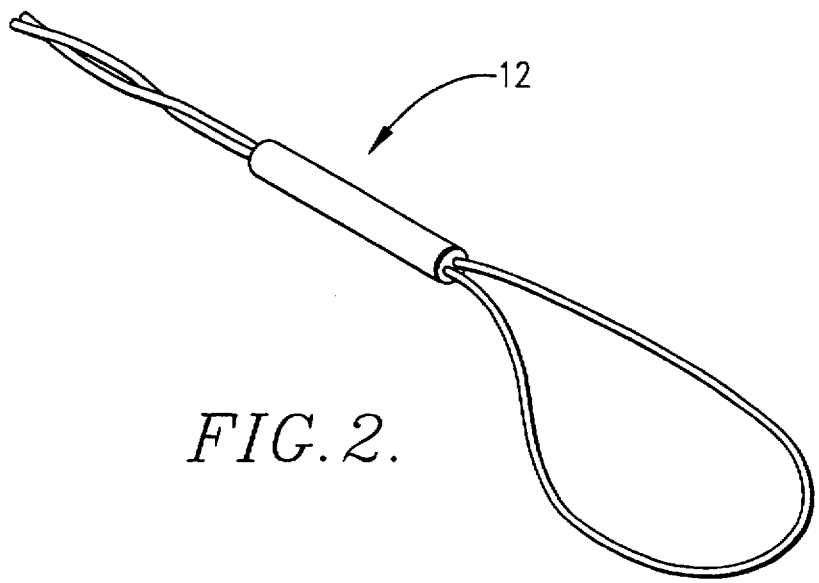

As best illustrated in FIG. 2, the preferred sensor is an indium-gallium strain gauge designed to be worn around a male patient's penis. The preferred sensor measures the circumference of the individual's penis for detecting changes in the sexual arousal of the individual.

Sensor 12 may also include other types of conventional physiological sensors such as a skin temperature sensor for sensing the individual's skin temperature, a blood pressure sensor for sensing the individual's blood pressure or a heart sensor for sensing the individual's heart rate. Sensor 12 may also include a vaginal wall reflectivity sensor that permits the apparatus 10 to be used with females.

Microprocessor 14 is coupled with sensor 12 for receiving the sensor signals generated by the sensor, converting the sensor signals to control signals representative of the sensor signals, and storing the control signals. As described in more detail below, microprocessor 14 periodically or continuously transfers the stored control signals to transmitter 16 for transmitting the control signals to an analyzing device remote from apparatus 10.

The preferred microprocessor 14 is a Micro 440e device manufactured by Blue Earth Research of Mankato, Minnesota and includes a time clock, an analog-to-digital converter, an LED numeric display, a serial data port, and internal memory. In an alternate embodiment of the invention, microprocessor 14 may includes a separate memory device coupled with the microprocessor.

Microprocessor 14 is controlled by a computer program stored in the microprocessor. One subroutine in the program dumps all the control signals from the microprocessor memory to the RS232 port of the microprocessor. Another subroutine clears the memory. Another subroutine of the program reads the sensor signals and converts the sensor signals to control signals, stores the control signals with a time/date stamp, displays the control signals on the LCD, drives audio feedback 20 and drives transmitter 16 as described below.

Microprocessor 14 may also be programmed for receiving and storing a pre-determined threshold signal representative of a threshold level of sexual arousal for the individual. Microprocessor 14 compares the control signals to the threshold signal and generates an alarm or monitoring signal whenever the control signals exceed the threshold signal to indicate that the individual's sexual arousal has exceeded the threshold arousal level.

In the preferred embodiment of the invention, the predetermined threshold signal corresponds to a threshold size of the individual's penis. To determine the threshold signal, the circumference of the individual's penis is first measured in its flaccid state, which corresponds to no sexual arousal, and then measured in its fully erect state, which corresponds to complete sexual arousal. The threshold signal is then chosen to be a percentage (e.g., 30%) of the fully erect measurement. Then, whenever sensor 12 senses that the circumference of the individual's penis exceeds the threshold circumference (i.e., the control signals are greater than the threshold signal), microprocessor 14 generates the alarm or monitoring signal.

The computer program is preferably written in Intel 51 Basic computer language. The source code for the computer program is reproduced in the attached Source Code Appendix.

Transmitter 16 is coupled with and responsive to microprocessor 14 for transmitting the control signals stored in the memory of the microprocessor to an analyzing device remote from apparatus 10. The analyzing device is controlled by a data analysis program that analyzes the control signals for use in monitoring the sexual arousal of the individual.

The preferred transmitter 16 is a conventional radio transceiver such as a Model 150R transceiver manufactured by Tri-Tronics, Inc., of Tucson, Ariz. Transmitter 16 may also include modem 26 coupled with an RS232 port of microprocessor 14 for modulating the control signals and for transmitting the modulated signals over a conventional telephone or cellular telephone. Modem 26 is preferably a 14.4 Kbps modem such as the Pocket Fax/Modem manufactured by CELLect.

Microprocessor 14 may be programmed for either continuously or periodically transmitting the control signals stored in the memory of the microprocessor. When the control signals are transmitted by a conventional radio transceiver such as the one described above, microprocessor 14 and transmitter 16 are preferably configured for continuously transmitting the control signals to the remote analyzing device since radio transceivers require little power. However, when the control signals are transmitted by a modem and telephone, microprocessor 14 and transmitter 16 are preferably configured for either periodically transmitting the control signals or transmitting only the alarm or monitoring signals described above since modems and telephones have greater power requirements.

In an alternate embodiment of the invention, apparatus 10 may not include a transmitter. Instead, the control signals may be initially stored in microprocessor 14 and periodically transferred to the analyzing device by downloading the control signals in a conventional manner rather than transmitting the control signals to the analyzing device.

Position detector 18 is operably coupled with microprocessor 14 for detecting the position or location of the individual wearing apparatus 10 and for generating position signals for delivery to the microprocessor. Microprocessor 14 either periodically or continuously dumps these position signals to transmitter 16 for transmitting the position signals to a remote monitoring station such as the analyzing device discussed above. The position signals are used to track the activities of the individual or to locate the individual whenever the transmitted control signals indicate that the individual has become sexually aroused.

The position detector 18 also permits the therapist or correctional professional to enter into the apparatus certain areas that the patient is prohibited from entering into. Then, if the individual enters these prohibited areas, the position detector 18 and the audio feed-back 20 described below cooperate to warn the individual that they are entering a prohibited area. The position detector may also be coupled with a clock so that the signal generated by the position detector can also be sent to a remote monitoring station if the individual does not leave the prohibited area within a specified amount of time.

The preferred position detector 18 is a conventional global positioning satellite (GPS) receiver such as a GPS XPRESS receiver manufactured by Allied Signal of Olathe, Kans. or an equivalent GPS receiver. The GPS receiver is operable for receiving satellite signals from a GPS satellite system and for calculating the position of apparatus 10 in accordance with the received position signals.

Audio feed-back 20 is coupled with microprocessor 14 and responsive to the alarm or monitoring signals generated by the microprocessor for providing an audible signal to the individual whenever the control signals generated by the microprocessor exceed the threshold signal entered into the microprocessor. This provides an audible signal to the individual whenever sensor 12 senses that the individual's sexual arousal level has exceeded the threshold arousal level. The individual can then be taught to reduce their arousal to whatever stimuli is causing the sexual arousal.

The preferred audio feed-back 20 is a conventional speaker or tone generator integrally formed with microprocessor 14. Alternately, audio feed-back 20 may be a stand-alone speaker or other tone generator electrically coupled with microprocessor 14.

Manually activated input 22 is coupled with microprocessor 14 for permitting the individual to input analog signals into the microprocessor for processing by the microprocessor. This permits the individual to assess his or her own sexual arousal level and to input an analog signal representative of this sexual arousal level into the microprocessor for self-reporting of their sexual arousal. The preferred manually activated input 22 is a conventional potentiometer or similar device.

Microprocessor 14 receives the analog input signals from manually activated input 22 and converts them to self-reported control signals similar to the control signals described above. These self-reported control signals are then transmitted to the remote analyzing device in the same manner as the control signals corresponding to the measured sensor signals.

As illustrated in FIG. 1, microprocessor 14 as well as the other components of apparatus 10 are preferably powered by a conventional DC battery 28. Apparatus 10 may also include amplifier 30 electrically coupled between sensor 12 and microprocessor 14 for amplifying the sensor signals generated by the sensor.

In operation, an individual being monitored by apparatus 10 is instructed to attach sensor 12 to the appropriate portion of the individual's body. For example, if the individual is male and sensor 12 is a plethysmograph, the individual is instructed to place the sensor over his penis. The remaining components of apparatus 10 may be stored in a fanny pack which is worn by the individual.

The individual is then exposed to real-life sexual stimuli in the individual's normal environment. For example, the individual may be taken to or instructed to visit locations where the therapist or correctional professional knows the individual will be exposed to sexual stimuli. Alternately, the individual may be merely instructed to go about his or her normal routine. In either case, the individual is eventually exposed to real-life sexual stimuli outside of a clinical or laboratory setting.

While the individual is being exposed to sexual stimuli, sensor 12 continuously senses physiological changes in the individual, such as changes in the circumference of the individual's penis, that correspond to the sexual arousal of the individual. Sensor 12 generates sensor signals representative of these physiological changes and transfers the signals through amplifier 30 and to microprocessor 14.

Microprocessor 14 converts the sensor signals to control signals and stores the control signals in its memory. Microprocessor 14 then directs transmitter 16 to either continuously or periodically transmit the stored control signals to the remote analyzing device for analyzing and monitoring the sexual arousal of the individual. Microprocessor 14 also directs transmitter 16 to continuously or periodically transmit the position signals generated by position detector 18 and directs audio feed-back 20 to provide an audible alarm signal whenever the individual's sexual arousal level has exceeded the threshold arousal level as determined by the entered threshold signal.

Although the invention has been described with reference to the preferred embodiment illustrated in the attached drawing figures, it is noted that equivalents may be employed and substitutions made herein without departing from the scope of the invention as recited in the claims. For example, although apparatus 10 has been described as primarily being used for detecting and monitoring of the sexual arousal of male sexual offenders, it may also be used with female sexual offenders and in the assessment and treatment of non-criminal sexual disorders such as impotence.

SOURCE CODE APPENDIX

Inventor: DE BRIERE, TERRY J., et al

Assignee: Parsons State Hospital Endowment Association, Inc.

Docket No. 25045

Title: APPARATUS AND METHOD FOR DETECTING AND MONITORING THE SEXUAL AROUSAL OF AN INDIVIDUAL BIOFEED 1Txt

```
1   REM BIOFEEDBACK

10   DIM C(20),A(8),L(20)

120  Y1=-1

150  REM READ CRITERIA FOR ALARM IN BITS
153  AL=XBY(24402)
161  IF AL<5 THEN AL=255
162  IF AL>60 THEN AL=255

200  REM READ IN DATA FOR LED
210  FOR X=0 TO 9
220  READ L(X)
230  NEXT X
240  PRINT "STARTING WATCHDOG"
250  FOR X=0 TO 2000
260  NEXT X
270  PRINT "WATCHDOG STARTED"
300  PCA=0 : CCAPM4=48H : CCAP4=0FFFFH : CMOD=40H : CCON=40H 3000 rem top of loop
3010 GOSUB 13000
3013 CCAP4=PCA
3020 GOSUB 12000
3025 CCAP4=PCA
3050 IF AL<A(7) THEN BP=1 ELSE BP=0

3130 IF SC=0.AND.SC<>LSC THEN GOSUB 12200
3131 CCAP4=PCA
3132 IF SC=3.AND.SC<>LSC THEN GOSUB 12200
3133 CCAP4=PCA
3134 IF SC=6.AND.SC<>LSC THEN GOSUB 12200
3135 CCAP4=PCA
3136 IF SC=9.AND.SC<>LSC THEN GOSUB 12200
3137 CCAP4=PCA
3138 IF SC=12.AND.SC<>LSC THEN GOSUB 12200
3139 CCAP4=PCA
3140 IF SC=15.AND.SC<>LSC THEN GOSUB 12200
3141 CCAP4=PCA
3142 IF SC=18.AND.SC<>LSC THEN GOSUB 12200
3143 CCAP4=PCA
3144 IF SC=21.AND.SC<>LSC THEN GOSUB 12200
3145 CCAP4=PCA
3146 IF SC=24.AND.SC<>LSC THEN GOSUB 12200
3147 CCAP4=PCA
3148 IF SC=27.AND.SC<>LSC THEN GOSUB 12200
3149 CCAP4=PCA
3150 IF SC=30.AND.SC<>LSC THEN GOSUB 12200
3151 CCAP4=PCA
3152 IF SC=33.AND.SC<>LSC THEN GOSUB 12200
3153 CCAP4=PCA
```

```
3154 IF SC=36 AND SC<>LSC THEN GOSUB 12200
3155 CCAP4=PCA
3156 IF SC=39 AND SC<>LSC THEN GOSUB 12200
3157 CCAP4=PCA
3158 IF SC=42 AND SC<>LSC THEN GOSUB 12200
3159 CCAP4=PCA
3160 IF SC=45 AND SC<>LSC THEN GOSUB 12200
3161 CCAP4=PCA
3162 IF SC=48 AND SC<>LSC THEN GOSUB 12200
3163 CCAP4=PCA
3164 IF SC=51 AND SC<>LSC THEN GOSUB 12200
3165 CCAP4=PCA
3168 IF SC=54 AND SC<>LSC THEN GOSUB 12200
3169 CCAP4=PCA
3170 IF SC=57 AND SC<>LSC THEN GOSUB 12200
3171 CCAP4=PCA
3180 LSC=SC
3181 CCAP4=PCA
3190 GOTO 3000

12000 REM  ANALOG TO DIGITAL CONV
12003 CCAP4=PCA
12010 C=14
12020 XBY(0FF00H)=C
12030 A(C-7)=XBY(0FF00H)
12063 CCAP4=PCA
12070 A(7)=INT(A(7)*100/192)
12075 L1=INT(A(7)/10)
12077 L2=A(7)-(L1*10)
12078 CCAP4=PCA
12090 RETURN

12200 REM  LOG DATA
12201 CCAP4=PCA
12202 MC=0
12203 IF HR<7 THEN PRINT "TOO EARLY" : RETURN
12204 CCAP4=PCA
12205 IF HR>16 THEN MC=1000
12206 IF ((HR*60)+MN)>1438 THEN PRINT "TOO LATE" : RETURN
12208 CCAP4=PCA
12210 S=INT(SC/3)
12220 KEEP=((HR+3)*1200)+(MN*20)+S-8000+MC
12240 XBY(KEEP)=A(7)
12245 CCAP4=PCA
12250 PRINT "LOG ENTRY AT ",KEEP,AL
12253 CCAP4=PCA
12260 IF KEEP>24400 THEN PRINT "END OF LOG" : END
12265 CCAP4=PCA
12290 RETURN

13000 REM read time clock
13010 GOSUB 13900
13020 CCAP4=PCA
13030 FOR X=0 TO 0CH
```

24

```
13035 CCAP4=PCA
13040 D=0FE00H+X*(10H)
13050 TC(X-1)=XBY(D).AND 0FH
13060 NEXT X
13065 CCAP4=PCA
13070 GOSUB 13800
13080 WKDAY=TC(A0H)
13100 PM=0
13105 IF TC(6)>1 THEN PM=1 : TC(6)=TC(6)-4
13110 HR=10*TC(6)+TC(5)
13120 MN=10*TC(4)+TC(3)
13130 SC=10*TC(2)+TC(1)
13140 IF (HR=12.AND.PM=0) THEN HR=0
13150 IF (HR>0.AND.PM=1) THEN HR=HR+12
13160 IF HR=24 THEN HR=12
13180 IF SC<>LSC THEN GOSUB 13300
13185 CCAP4=PCA
13190 RETURN

13300 REM PRINT ROUTINE AND LED DISPLAY
13310 Y1=Y1+1
13315 CCAP4=PCA
13320 PRINT "TIME ",HR,":",MN,":",SC," AROUSAL=",A(7),Y1
13322 IF Y1>2 THEN Y1=0
13323 IF Y1=1 THEN PORT1=L(L1)
13324 IF Y1=2 THEN PORT1=L(L2)
13325 IF Y1=0 THEN PORT1=NOT(G).AND.0FFH
13335 CCAP4=PCA
13336 CCON=0H
13340 IF (Y1=0.AND.BP=1) then PWM 100,100,2200
13350 PCA=0 : CCAPM4=48H : CCAP4=0FFFFH : CMOD=40H : CCON=40H
13360 CCAP4=PCA

13390 RETURN

13800 REM PUT RTC BACK TO NORMAL
13801 CCAP4=PCA
13810 BYTE=XBY(0FED0H).AND.0EH
13820 XBY(0FED0H)=BYTE
13821 CCAP4=PCA
13830 RETURN

13900 REM CHECK FOR RTC NOT BUSY
13901 CNT=0
13903 CCAP4=PCA
13910 BYTE=XBY(0FED0H)
13915 BYTE=(BYTE.AND.0EH)+1
13920 XBY(0FED0H)=BYTE
13923 CCAP4=PCA
13930 BYTE=XBY(0FED0H)
13940 IF (BYTE.AND.2)=0 THEN RETURN
13943 CCAP4=PCA
```

```
13950 XBY(0FED0H)=(BYTE.AND.0EH)
13960 CNT=CNT+1
13970 IF CNT>1000 THEN RETURN
13973  CCAP4=PCA
13980 GOTO 15910

15900 DATA 24,252,73,200,172,138,10,248,8,168
```

Dump.Txt

2 REM DUMP PLETHYSMOGRAPH DATA

9 Print " Did you rembember to select TRANSFER ?"
10 print " Did you select RECIEVE TEXT FILE ?"
11 print " Did you enter a file name?"
12 print " Did you add the .CSV extension?"
13 print
14 print "IF you did the above, press 5 "
15 print "If you didn't, do it NOW before pressing enter"
16 input a 15001 CCON=0H
15010 J=4000 : F2=0
15020 IF J<16001 THEN GOSUB 15400
15030 IF J>16999 THEN GOSUB 15500
15040 PRINT H1,",",M1,",",S1,",",XBY(J)
15050 IF XBY(J)>0 THEN F2=0
15060 IF J=16000 THEN J=17000
15070 J=J+1
15080 IF J<24400 THEN GOTO 15020
15110 END 15400 H1=INT((J+8000)/1200)
15415 CCAP4=PCA
15420 M1=J-((H1*1200)-8000)
15430 M1=INT(M1/20)
15440 S1=J-(((H1*1200)-8000)+M1*20)
15443 CCAP4=PCA
15450 S1=S1*3 : H1=H1-3
15460 RETURN 15500 H1=INT((J+7000)/1200)
15515 CCAP4=PCA
15520 M1=J-((H1*1200)-7000)
15530 M1=INT(M1/20)
15540 S1=J-(((H1*1200)-7000)+M1*20)
15550 S1=S1*3 : H1=H1-3
15553 CCAP4=PCA
15560 RETURN Clearmem.Txt

```
4 REM Warning this program clears memory ''

100 print "WARNING, YOU ARE ABOUT TO CLEAR MEMORY !!"
120 PRINT
130 PRINT "PRESS 9 TO CLEAR MEMORY,  ANY OTHER NUMBER TO ABORT !!"
140 INPUT Q
150 IF Q<>9 THEN PRINT "PROGRAM ABORTED, MEMORY NOT CLEARED":END
14000 REM RESET KEEP AND CLEAR MEMORY
14055 PRINT "CLEARING MEMORY"
14060 FOR I=4000 TO 16000 : XBY(I)=0 : NEXT I
14061 PRINT "HALF WAY DONE, HAVE PATIENCE"
14062 FOR I=16995 TO 24401 : XBY(I)=0 : NEXT I
14065 PRINT "MEMORY IS CLEAR"
14070 END
```

We claim:

1. An apparatus for detecting and monitoring the sexual arousal of an individual, said apparatus comprising:

sensing means for sensing physiological changes in the individual that correspond to the sexual arousal of the individual and for generating sensor signals representative of the physiological changes;

computing means coupled with said sensing means for receiving said sensor signals, for converting said sensor signals to control signals representative of the sensor signals, and for storing said control signals;

transferring means coupled with and responsive to said computing means for transferring said control signals stored in said computing means to an analyzing device remote from said apparatus for analyzing said control signals to monitor the sexual arousal of the individual; and attaching means for releaseably attaching said sensing means, said computing means, and said transferring means directly to the individual for permitting the individual to move unrestrictedly while the apparatus remains operably attached to the individual.

2. The apparatus as set forth in claim 1, said transferring means including transmitting means for transmitting said control signals to the analyzing device.

3. The apparatus as set forth in claim 2, said computing means including means for periodically transferring said stored control signals to said transmitting means for periodically transmitting said control signals to the analyzing device.

4. The apparatus as set forth in claim 2, said computing means including means for continuously transferring said stored control signals to said transmitting means for continuously transmitting said control signals to the analyzing device.

5. The apparatus as set forth in claim 2, said transmitting means including a radio transceiver.

6. The apparatus as set forth in claim 2, said transmitting means including a modem coupled with said computing means for modulating said control signals and a telephone coupled with said modem for transmitting said modulated control signals to the analyzing device.

7. The apparatus as set forth in claim 1, said computing means further including means for receiving and storing a pre-determined threshold signal corresponding to a pre-determined level of change in a physiological parameter of the individual, comparing means for comparing said control signals to said threshold signal, and alarm signal generating means for generating an alarm signal when said control signals exceed said threshold signal.

8. The apparatus as set forth in claim 7, further including audio means coupled with said computing means and responsive to said alarm signal for providing an audible signal whenever said control signals exceed said threshold signal.

9. The apparatus as set forth in claim 8, said audio means including a speaker.

10. The apparatus as set forth in claim 2, further including position detecting means coupled with said computing means for detecting the position of the individual, for generating position signals representative of the position of the individual, and for transferring said position signals to said computing means.

11. The apparatus as set forth in claim 10, said computing means including means for periodically transferring said position signals to said transmitting means for periodically transmitting said position signals to the analyzing device.

12. The apparatus as set forth in claim 10, said computing means including means for continuously transferring said position signals to said transmitting means for continuously transmitting said position signals to the analyzing device.

13. The apparatus as set forth in claim 10, said position detecting means including a global positioning satellite receiver operable for receiving satellite signals from a global positioning satellite system and for calculating the position of said receiver in accordance with the satellite signals.

14. The apparatus as set forth in claim 1, further including manually activated analog input means coupled with said computing means for permitting the individual to assess his or her own sexual arousal level and to input an analog signal representative of the sexual arousal level into said computing means.

15. The apparatus as set forth in claim 14, said manually activated analog input means including a potentiometer.

16. The apparatus as set forth in claim 1, further including amplifying means coupled between said sensing means and said computing means for amplifying said sensor signals.

17. The apparatus as set forth in claim 1, the individual being male, said physiological changes including changes in the size of the individual's penis, said sensing means including a penile plethysmograph.

18. The apparatus as set forth in claim 1, said physiological changes including changes in the skin temperature of the individual, said sensing means including a skin temperature sensor.

19. The apparatus as set forth in claim 1, said physiological changes including changes in the blood pressure of the individual, said sensing means including a blood pressure sensor.

20. The apparatus as set forth in claim 1, said physiological changes including changes in the heart rate of the individual, said sensing means including a heart rate sensor.

21. The apparatus as set forth in claim 1, said computing means including a microprocessor having internal memory.

22. The apparatus as set forth in claim 1, said computing means including a microprocessor and a memory device coupled with said microprocessor.

23. A method of detecting and monitoring the sexual arousal of an individual, said method comprising the steps:

attaching a physiological sensor to the individual;

releasably attaching a computing means and a transmitting means directly to the individual and coupling the computing means with said physiological sensor;

sensing with said physiological sensor physiological changes in the individual that correspond to the sexual arousal of the individual and generating sensor signals representative of the physiological changes with said physiological sensor;

transferring said sensor signals to said computing means for converting said sensor signals to control signals representative of the sensor signals and for storing said control signals;

periodically transferring said stored control signals to said transmitting means for transmitting said stored control signals to an analyzing device remote from said computing means; and analyzing said control signals with said analyzing device to monitor the sexual arousal of the individual.

24. The method as set forth in claim 23, said transmitting means including a radio transceiver for transmitting said control signals to said analyzing device.

25. The method as set forth in claim 23, said transmitting means including a modem coupled with said computing means for modulating said control signals and a telephone coupled with said modem for transmitting said modulated control signals to said analyzing device.

26. The method as set forth in claim 23, further including the steps of receiving and storing in said computing means a pre-determined threshold signal corresponding to a pre-determined level of change in a physiological parameter of the individual, comparing said control signals to said threshold signal, and generating an alarm signal when said control signals exceed said threshold signal.

27. The method as set forth in claim 26, further including the step of generating an audible alarm signal with an audio means coupled with said computing means whenever said control signals exceed said threshold signal.

28. The method as set forth in claim 27, said audio means including a speaker.

29. The method as set forth in claim 23, further including the steps of detecting the position of the individual with a position detecting means coupled with said computing means, generating position signals representative of the position of the individual, and transmitting said position signals to said analyzing device for monitoring the location of the individual or providing feed-back to the individual if the individual is in a prohibited location.

30. The method as set forth in claim 29, said position detecting means including a global positioning satellite receiver operable for receiving satellite signals from a global positioning satellite system and for calculating the position of said receiver in accordance with the satellite signals.

31. The method as set forth in claim 23, further including the steps of permitting the individual to assess his or her own sexual arousal level with a manually activated analog input means coupled with said computing means and to input an analog signal representative of the sexual arousal level into said computing means.

32. The method as set forth in claim 31, said manually activated analog input means including a potentiometer.

33. The method as set forth in claim 23, further including the step of amplifying said sensor signals with an amplifying means coupled between said sensing means and said computing means.

34. The method as set forth in claim 23, the individual being male, said physiological changes including changes in the size of the individual's penis, said sensing means including a penile plethysmograph.

35. The method as set forth in claim 23, said physiological changes including changes in the skin temperature of the individual, said sensing means including a skin temperature sensor.

36. The method as set forth in claim 26, said physiological changes including changes in the blood pressure of the individual, said sensing means including a blood pressure sensor.

37. The apparatus as set forth in claim 26, said physiological changes including changes in the heart rate of the individual, said sensing means including a heart rate sensor.

38. The method as set forth in claim 23, said computing means including a microprocessor having internal memory.

39. The method as set forth in claim 23, said computing means including a microprocessor and a memory device coupled with said microprocessor.

* * * * *